United States Patent
Klee et al.

(10) Patent No.: US 6,812,266 B2
(45) Date of Patent: Nov. 2, 2004

(54) HYDROLYSIS STABLE ONE-PART SELF-ETCHING, SELF-PRIMING DENTAL ADHESIVE

(75) Inventors: Joachim E. Klee, Radolfzell (DE); Uwe Walz, Konstanz (DE)

(73) Assignee: Dentsply DeTrey GmbH (DE)

( * ) Notice: Subject to any disclaimer, the term of this patent is extended or adjusted under 35 U.S.C. 154(b) by 75 days.

(21) Appl. No.: 10/213,303

(22) Filed: Aug. 6, 2002

(65) Prior Publication Data

US 2003/0055124 A1 Mar. 20, 2003

Related U.S. Application Data

(60) Provisional application No. 60/311,433, filed on Aug. 10, 2001.

(51) Int. Cl.$^7$ ................................. C08F 2/46
(52) U.S. Cl. ................ 522/171; 522/173; 522/175; 522/178; 522/182; 522/908; 522/48; 522/71; 522/74; 522/81; 522/150; 522/152; 522/153; 523/109; 523/105; 523/118; 523/115
(58) Field of Search .................. 522/48, 71, 74, 522/81, 150, 153, 152, 173, 178, 175, 182, 908; 523/105, 109, 118, 115

(56) References Cited

U.S. PATENT DOCUMENTS

| | | | |
|---|---|---|---|
| 4,089,763 A | 5/1978 | Dart et al. | 204/159.23 |
| 4,386,912 A | 6/1983 | Nagase et al. | 433/228 |
| 4,485,211 A | 11/1984 | Okamoto | 525/57 |
| 4,539,382 A * | 9/1985 | Omura et al. | 526/276 |
| 4,558,120 A | 12/1985 | Tomalia et al. | 528/363 |
| 4,587,329 A | 5/1986 | Tomalia et al. | 528/363 |
| 4,857,599 A | 8/1989 | Tomalia et al. | 528/259 |
| 4,938,885 A | 7/1990 | Migdal | 252/51.5 |
| 5,192,815 A | 3/1993 | Okada et al. | 523/115 |
| 5,229,244 A | 7/1993 | Hertler et al. | 430/176 |
| 5,274,064 A | 12/1993 | Sarkar | 528/25 |
| 5,395,883 A | 3/1995 | Yates, III et al. | 525/89 |
| 5,418,301 A | 5/1995 | Hult et al. | 525/437 |
| 5,530,092 A | 6/1996 | Meijer et al. | 528/363 |
| 5,591,809 A | 1/1997 | Vicari et al. | 525/419 |
| 5,847,025 A | 12/1998 | Moszner et al. | 523/116 |
| 5,925,690 A | 7/1999 | Fuchigami et al. | 523/118 |
| 5,969,000 A | 10/1999 | Yang et al. | 523/116 |
| 5,985,958 A | 11/1999 | Moszner et al. | 524/83 |
| 6,147,137 A * | 11/2000 | Jia | 523/118 |
| 6,174,935 B1 | 1/2001 | Matsunae et al. | 523/118 |
| 6,592,372 B2 * | 7/2003 | Jia et al. | 433/215 |

FOREIGN PATENT DOCUMENTS

| | | |
|---|---|---|
| DE | 3703080 | 1/1988 |
| DE | 3703120 | 1/1988 |
| DE | 3903407 | 8/1990 |
| DE | 4133494 | 4/1993 |
| EP | 023686 | 2/1981 |
| EP | 049559 | 4/1982 |
| EP | 059649 | 9/1982 |
| EP | 102199 | 3/1984 |
| EP | 140140 | 5/1995 |
| EP | 682059 | 11/1995 |
| EP | 716103 | 6/1996 |
| EP | 783880 | 7/1997 |
| EP | 0811368 | 12/1997 |
| EP | 1057468 | 12/2000 |
| SU | 334845 | 10/1989 |
| WO | 93/14147 | 7/1993 |
| WO | 93/18079 | 9/1993 |
| WO | 96/07688 | 3/1996 |
| WO | 02/02057 | 1/2002 |

OTHER PUBLICATIONS

A.R. Kannurpatti et al., Polym. Prep. 38 (1997) 106.
W.D. Cook et al., Dent. Mat 15 (1999) 447.
P.A. Liso et al., Biomaterials 18 (1997) 15.
A.T. Diplock et al., Br. J. Nutr. 80 (1998), Suppl 1, 77.
L. O.thompson, Crit. Rev. Food Sci. Nutr. 34 (1994), 473.
W.D. Cook et al; "Cure of Resin based Restorative Materials II White Light Photo–polymerized Resins" Australian Dental Journal, vol. 28, No. 5, Oct. 1983.
L. Shajii, J.P. Santerre, Biomaterials 20 (1999) 1897.
W.R. Hume, T.M. Gerzia, Crit. Rev. Oral. Biol. Med. 7 (1996) 172).

* cited by examiner

Primary Examiner—James J. Seidleck
Assistant Examiner—Sanza L. McClendon
(74) Attorney, Agent, or Firm—Douglas J. Hura; James B. Bieber

(57) ABSTRACT

A dental adhesive composition for bonding dental restoratives to dentin and enamel provides a one-part self-etching, self-priming dental adhesive composition having hydrolysis stable polymerizable acidic adhesive monomers.

3 Claims, No Drawings

HYDROLYSIS STABLE ONE-PART SELF-ETCHING, SELF-PRIMING DENTAL ADHESIVE

This application claims benefit of 60/311,433 filed Aug. 10, 2001.

TECHNICAL FIELD

The invention relates to dental adhesive compositions for bonding dental restoratives to dentin and enamel. More specifically the invention provides a one-part self-etching, self-priming dental adhesive composition comprising hydrolysis stable polymerizable acidic adhesive monomers.

BACKGROUND OF THE INVENTION

Presently, self-etching, self-priming dental adhesives are composed of two-part systems due to stability issues of the polymerizable acidic monomers The stability issues are due to the hydrolysis of acidic and adhesive monomers in water or water/solvent mixtures. Therefore the acidic and adhesive monomers are stored water-free and mixed with the aqueous part just before application Frequently, sulfuric acid ester or phosphorous ester groups are employed in acidic polymerizable adhesive monomers. These acidic groups tend to hydrolyze ester moieties within of the monomers. To overcome these disadvantages polymerizable phosphonic esters were proposed (DE 19918974). However, these monomers still comprise hydrolysable (meth)acrylic ester moieties. Recently, hydrolysis stable monomers with phosphonic acid ester groups based on a-(oxo ethyl) acrylate were claimed (DE 19746708). However, the synthesis of these monomers is rather expensive and cost prohibitive for the envisaged applications.

Two-part self-etching, self-priming dental adhesive systems are either applied sequentially or in one step after mixing the two parts. Both procedures have inherent disadvantages due to clinical complications which might occur inbetween sequential steps (saliva or blood contamination) or due to dosing problems when mixing is required prior to the application of the self-etching adhesive.

In order to overcome these clinical problems it would be advantageous to provide the self-etching adhesive as a one-part system eliminating the need of sequential application or premixing.

DESCRIPTION OF THE PREFERRED EMBODIMENTS

The present invention provides a hydrolysis stable one-part self-etching, self-priming dental adhesive based on (meth)acrylamides and use thereof in polymerizable dental adhesive compositions containing i) a polymerizable (meth) acrylamide that comprises at least an organic or inorganic acidic moiety ii) a polymerizable monomer iii) polymerization initiator, inhibitor and stabilizer.

Preferably the hydrolysis stable one-part self-etching, self-priming dental adhesive comprises at least a carboxylic acid, a phosphoric acid or a sulfuric acid group or most preferably at least a phosphonic or a sulfonic acid moiety.

The polymerizable (meth) acrylamide that comprises at least a phosphonic or sulfonic acid moiety is characterized by the following formulas:

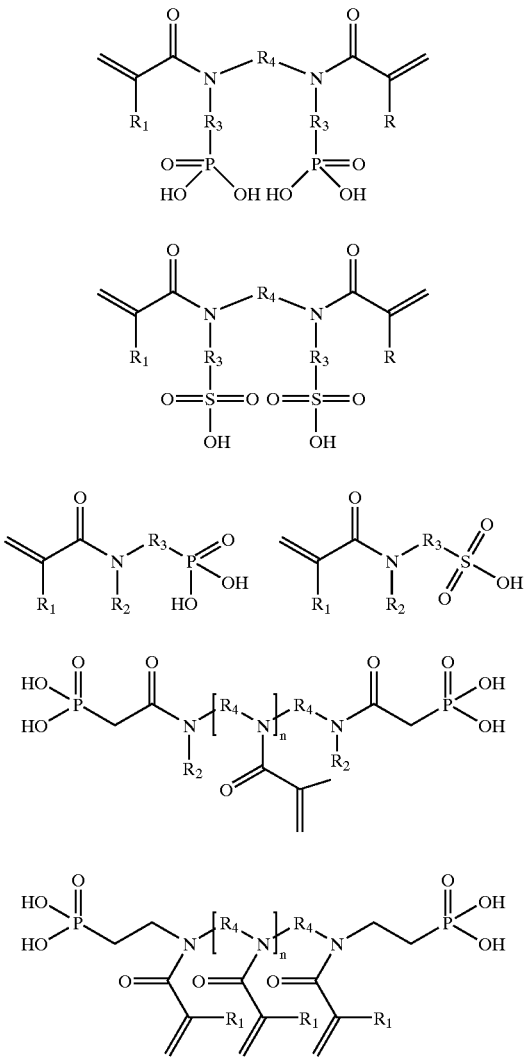

wherein $R_1$ and $R_2$ independently are Hydrogen or a substituted or unsubstituted $C_1$ to $C_{18}$ alkylene, substituted or unsubstituted cycloalkylene, substituted or unsubstituted $C_5$ to $C_{18}$ arylene or heteroarylene, substituted or unsubstituted $C_5$ to $C_{18}$ alkylarylene or alkylheteroarylene, substituted or unsubstituted $C_7$ to $C_{30}$ alkylene arylene, $R_3$ and $R_2$ independently are a difunctional substituted or unsubstituted $C_1$ to $C_{18}$ alkylene, difunctional substituted or unsubstituted cycloalkylene, difunctional substituted or unsubstituted $C_5$ to $C_{18}$ arylene or heteroarylene, difunctional substituted or unsubstituted $C_5$ to $C_{18}$ alkylarylene or alkylheteroarylene, difunctional substituted or unsubstituted $C_7$ to $C_{30}$ alkylene arylene, n is an integers.

In addition to the polymerizable (meth) acrylamide that comprises at least a phosphonic or sulfonic acid moiety polymerizable monomers are applied that also have an improved hydrolysis stability, that are characterized by the following formulas:

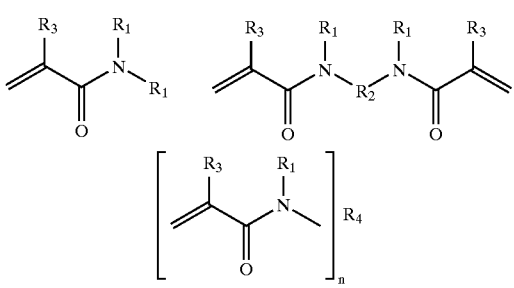

wherein

R₁ and R₃ independently are H or a substituted or unsubstituted $C_1$ to $C_{18}$ alkylene, substituted or unsubstituted cycloalkylene, substituted or unsubstituted $C_5$ to $C_{18}$ arylene or heteroarylene, substituted or unsubstituted $C_5$ to $C_{18}$ alkylarylene or alkylheteroarylene, substituted or unsubstituted $C_7$ to $C_{30}$ alkylene arylene, R₂ is a difunctional substituted or unsubstituted $C_1$ to $C_{18}$ alkylene, difunctional substituted or unsubstituted cycloalkylene, difunctional substituted or unsubstituted $C_5$ to $C_{18}$ arylene or heteroarylene, difunctional substituted or unsubstituted $C_5$ to $C_{18}$ alkylarylene or alkylheteroarylene, difunctional substituted or unsubstituted $C_7$ to $C_{30}$ alkylene arylene, R₄ is a mono- or polyfunctional substituted or unsubstituted $C_1$ to $C_{18}$ alkylene, mono- or polyfunctional substituted or unsubstituted cycloalkylene, mono- or polyfunctional substituted or unsubstituted $C_5$ to $C_{18}$ arylene or heteroarylene, mono- or polyfunctional substituted or unsubstituted $C_5$ to $C_{18}$ alkylarylene or alkylheteroarylene, mono- or polyfunctional substituted or unsubstituted $C_7$ to $C_{30}$ alkylene arylene, n is an integers.

The preferably used bis- and mono (meth) acrylamides are characterized by the following formulas:

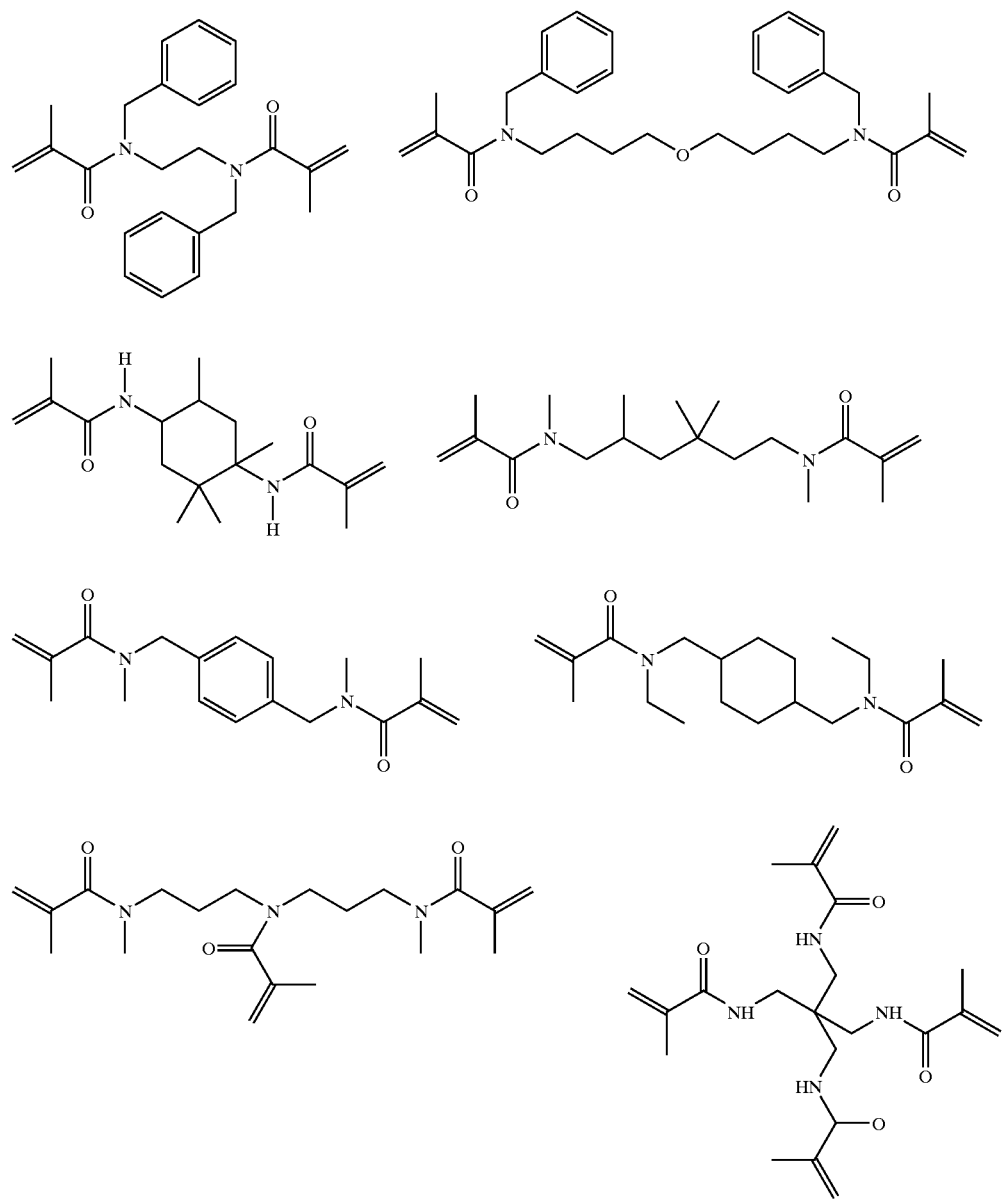

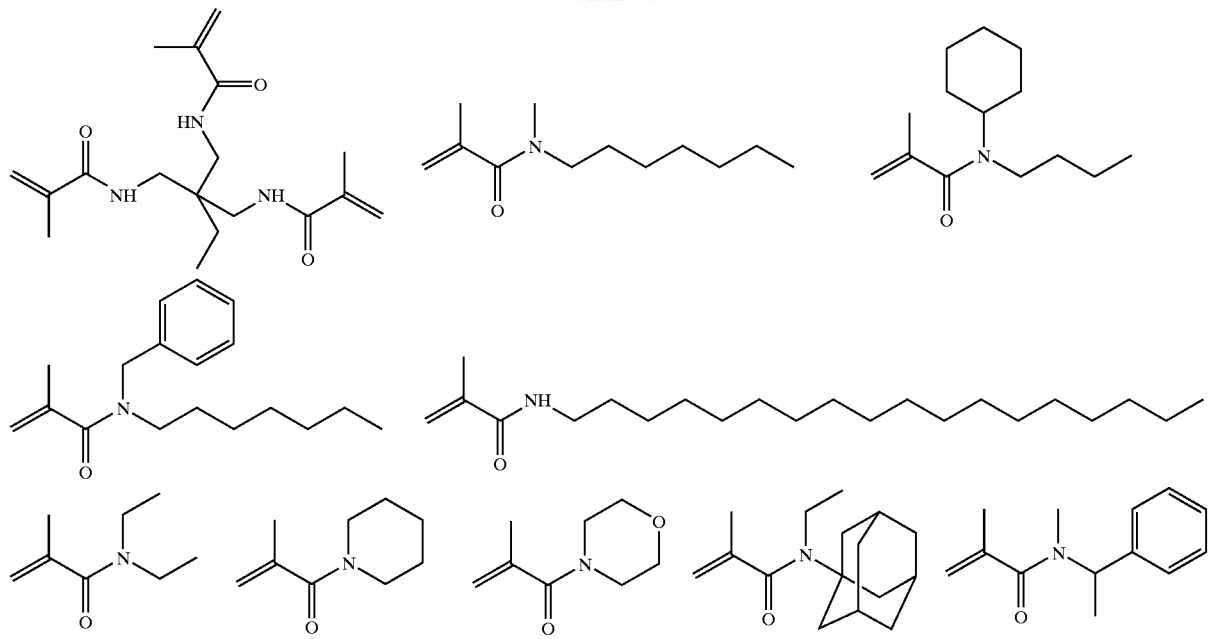

The claimed compositions comprise at least a bis- or poly(meth) acrylamide, a polymerizable mono acrylamide, an initiator, a stabilizer, water and/or an organic solvent.

The polymerization initiator is a thermal initiator, a redox-initiator or a photo initiator preferably used is champhor quinone. To stabilize the dental composition as stabilizer are applied radical absorbing monomers such as hydroquinone monomethylether, 2,6-di-tert.-butyl-p-cresol, tetramethyl piperidine N-oxyl radical, galvanoxyl radical.

EXAMPLE 1
N,N'-Bis (diethyl ethyl phosphonate)-1.2-Bis (2-aminoethoxy) ethane:

To 11.287 g (0.076 mol) 1.2-Bis (2-aminoethoxy) ethane were added 25.000 g (0.152 mol) Diethyl vinylphosphonate and stirred for 6 hours at 23° C.

Yield: 36.287 g (100% d. Th) ($C_{18}H_{42}O_8N_2P_2$), 476.49
IR: 3411, 3390 (OH), 2973, 2929, 2885 ($CH_2/CH_3$), 1390 ($CH_2/CH_3$), 1078 cm$^{-1}$ (OH).
$^{13}$C-NMR: 72.1 (6), 70.6 (7), 62.3 (2), 49.9 (5), 34.2 (4), 27.8 (3), 16.4 (1)

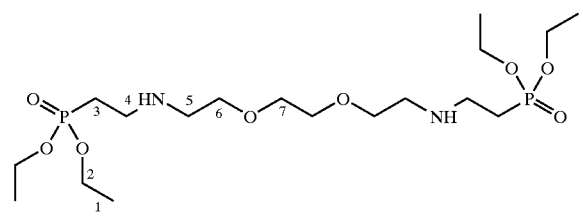

N,N'-Bis (diethyl ethyl phosphonate)-N,N'-bismethacrylamido-1.2-Bis (2-aminoethoxy) ethane:

In a 4-necked 1-l-flask equipped with a stirrer, a thermometer and two 50 ml dropping funnels 30.000 g (0.063 mol) of N,N'-Bis (diethyl ethyl phosphonate)-1.2-Bis (2-aminoethoxy) ethane were dissolved in 300 ml of methylene chloride. After cooling to 0–5° C. 13.164 g (0.126 mol) of methacryloyl chloride dissolved in 30 ml of methylene chloride and 5.036 g (0.126 mol) of NaOH dissolved in 15.106 ml of water were added simultaneously under stirring during 1.5 hours so that the temperature remains at 0–5° C. Thereafter the mixture were stirred at room temperature for additional two hours. Than the reaction mixture were hydrolyzed with 60 ml of ice-water. The organic phase were separated and the aqueous solution were extracted twice with methylene chloride. The collected organic liquids were washed with 50 ml of 1 n HCl, 50 ml of 1 n NaHCO$_3$ and sometimes with 50 ml of deionised water until the water shows a pH-value of approximately 7. Than the organic solution was dried over NaSO$_4$. Thereafter the NaSO$_4$ was filtered off and to the solution 0.039 g of 2,6-di-tert.-butyl-p-cresol were added. The methylene chloride was removed at 40° C. in vacuum and the bismethacrylamide was dried.

Yield: 32 g (83% of th.) ($C_{26}H_{50}O_{10}N_2P_2$), 612.64
$^{13}$C-NMR:167.7 (8), 140.2 (9), 121.7 (11), 70.6 (6), 69.4 (7), 62.3 (2), 48.2 (5), 32.5 (4), 25.1 (3), 19.3 (10), 16.4 (1)

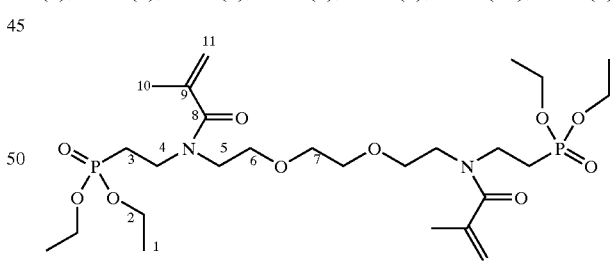

N,N'-Bis (ethyl phosphonic acid)-N,N'-bismethacrylamido-1.2-bis (2-aminoethoxy) ethane:

In a 4-necked 1-l-flask equipped with a stirrer, a thermometer, reflux cooler with CaCl$_2$-drying tube and 50 ml dropping funnels 30.000 g (0.049 mol) of N,N'-Bis (diethyl ethyl phosphonate)-N,N'-bismethacrylamido-1.2-Bis (2-aminoethoxy) ethane were dissolved in 100 ml of methylene chloride. Then 16.494 g (0.108 mol) Trimethyl bromsilane were added dropwise over an period of 20 minutes under stirring. Thereafter the reaction mixture was stirred for additional 2 hours. By adding of 100 methanol the phosphonic acid silylesters were hydrolyzed. Prior to remove the solvents BHT was added and the product was dried at 40° C. in vacuum.

Yield: 19.11 g (78.0% d. Th) ($C_{18}H_{34}O_{10}N_2P_2$), 500.42

$^{13}$C-NMR: 164.7 (8), 140.2 (9), 121.7 (11), 70.6 (7), 69.4 (6), 48.2 (5), 31.9 (4), 29.5 (3), 19.3 (10)

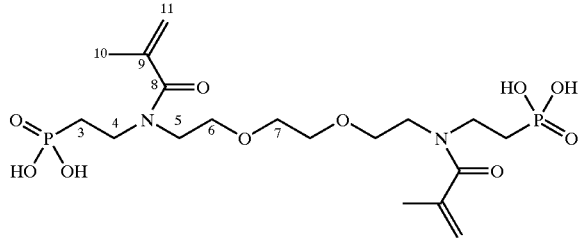

EXAMPLE 2
(Bis(3-methacyloylamidopropyl) diethylphosphonic acid ethylester:

58.073 g (0.443 mol) Bis(3-aminopropyl)amine, 184.454 g (0.894 mol) Dicyclohexyl carbodiimide and 8.651 g (0.071 mol) dimethylamino pyridine were dissolved in a mixture of 250 ml $CH_2Cl_2$ and 100 ml Acetone. To the cooled mixture (<5° C.) were added 76.200 g (0.885 mol) Methacrylic acid dissolved in 100 ml $CH_2Cl_2$ so that temperature do not pass 10° C. Then the mixture were stirred for 15 minutes at 0° C. and for 20 hours at room temperature. Thereafter the reaction mixture was cooled again and 92.227 g (0.447 mol) Dicyclohexyl carbodiimid dissolved in a mixture of 50 ml $CH_2Cl_2$ and 50 ml Acetone were added. To this mixture was dropped a solution of 86.804 g (0.443 mol) Diethylphosphonic acid ethylester dissolved in 100 ml Acetone so that temperature do not pass 10° C. Then the mixture were stirred for 15 minutes at 0° C. and for 20 hours at room temperature. After this time the precipitated solid was filtered off. To the filtrate were added 0.101 g BHT and the solvent was removed by vacuum distillation. The viscose residue was dissolved in 300 ml $CH_2Cl_2$ and cooled to 0° C. The precipitating solid was removed and the filtrate was washed twice with 150 ml 1 n HCl, 150 ml 1 n $NaHCO_3$ solution and with 150 ml water. Furthermore, the solution was dried over $NaSO_4$ and the solvent was removed. Than the solid was dissolved in Acetone again and dicyclohexyl urea was filtered of. Prior to remove the solvent, 0.197 g BHT was added, the product was dried in vacuum.

Yield: 155.7 g (79.0% of th.) ($C_{20}H_{36}N_3O_6P$), 445.50

IR: 3010/2933/2856 ($CH_2/CH_3$), 1695 (CO), 1653/1627 (C=C), 1452 ($CH_2/CH_3$), 1251 $cm^{-1}$ $^{13}$C-NMR: 169.1 (4), 166.5 (8), 140.2 (10), 121.7 (11), 61.6 (2), 44.6 (5), 43.0 (7), 27.9 (6), 27.7 (3), 19.0 (9), 16.4 (1)

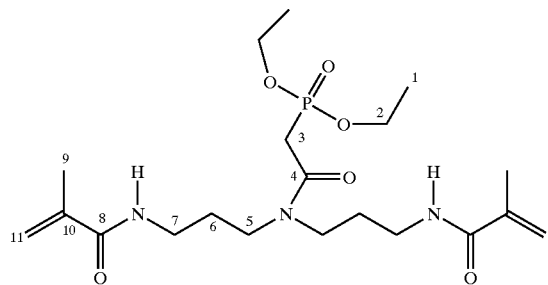

(Bis(3-methacyloylamidopropyl) diethylphosphonic acid:

In a 4-necked 1-l-flask equipped with a stirrer, a thermometer, reflux cooler with $CaCl_2$-drying tube and 100 ml dropping funnel 155.700 g (0.350 mol) of (Bis(3-methacyloylamidopropyl) diethylphosphonic acid ethylester were dissolved in 100 ml of methylene chloride. Then 117.77 g (0.769 mol) Trimethyl bromsilane were added dropwise over an period of 60 minutes under stirring. Thereafter the reaction mixture was stirred for additional 2 hours. By adding of 250 methanol the phosphonic acid silylesters were hydrolyzed. Prior to remove the solvents 0.157 g BHT were added and the product was dried at 40° C. in vacuum.

Yield: 115.0 g (84.5% d. Th) ($C_{16}H_{28}O_6N_3P$), 389.39

$^{13}$C-NMR: 169.1 (4), 166.5 (8), 140.2 (10), 121.7 (11), 44.6 (5), 43.0 (7), 27.9 (6), 32.1 (3), 19.0 (9)

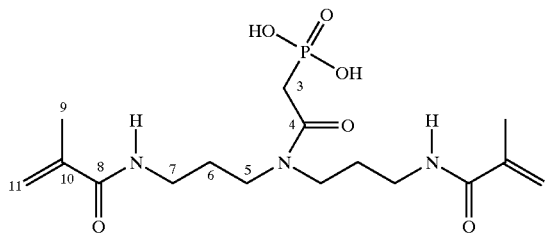

We claim:

1. Hydrolysis stable one-part self-etching, self-priming dental adhesive comprising (i) an acidic polymerizable (meth) acrylamide that comprises at least an organic or inorganic acidic moiety (ii) a polymerizable monomer -p1 (iii) polymerization initiator, inhibitor and stabilizer; wherein said polymerizable (meth) acrylamide is seletected from the group consisting of:

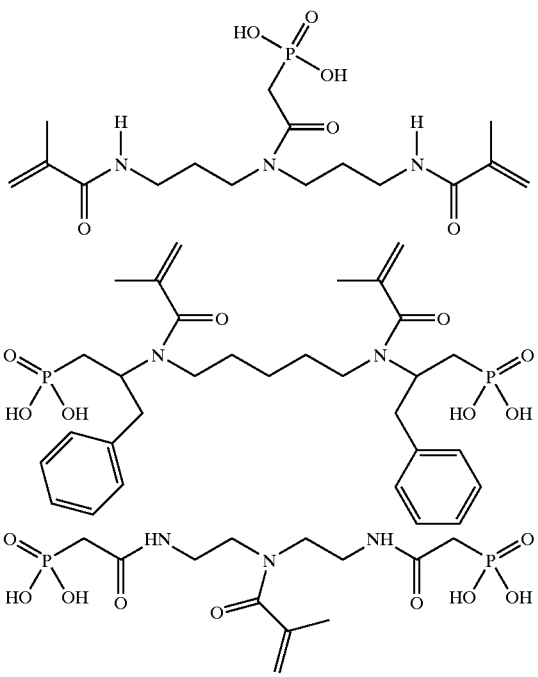

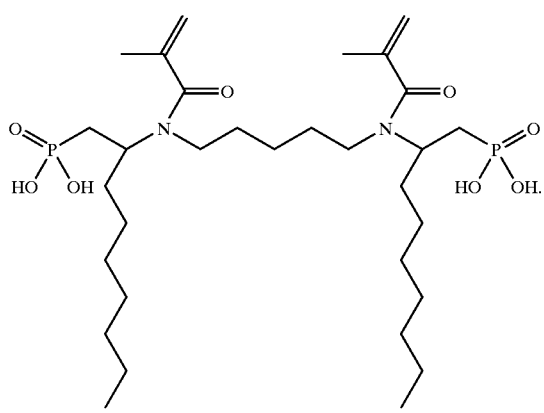

2. Hydrolysis stable one-part self-etching, self-priming dental adhesive comprising (i) an acidic polymerizable (meth) acrylamide that comprises at least an organic or inorganic acidic moiety (ii) a polymerizable monomer (iii) polymerization initiator, inhibitor and stabilizer; wherein said polymerizable monomer is selected from the group consisting of:

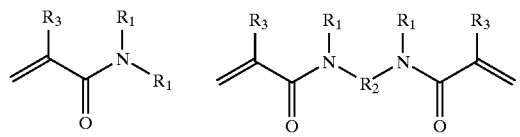

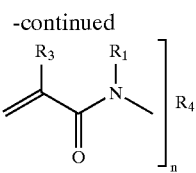

wherein
- $R_1$ and $R_3$ independently are H or a substituted or unsubstituted $C_1$ to $C_{18}$ alkylene, substituted or unsubstituted cycloalkylene, substituted or unsubstituted $C_5$ to $C_{18}$ arylene or heteroarylene, substituted or unsubstituted $C_5$ to $C_{18}$ alkylarylene or alkylheteroarylene, substituted or unsubstituted $C_7$ to $C_{30}$ alkylene arylene,
- $R_2$ is a difunctional substituted or unsubstituted $C_1$ to $C_{18}$ alkylene, difunctional substituted or unsubstituted cycloalkylene, difunctional substituted or unsubstituted $C_5$ to $C_{18}$ arylene or heteroarylene, difunctional substituted or unsubstituted $C_5$ to $C_{18}$ alkylarylene or alkylheteroarylene, difunctional substituted or unsubstituted $C_7$ to $C_{30}$ alkylene arylene, $R_4$ is a mono- or polyfunctional substituted or unsubstituted $C_1$ to $C_{18}$ alkylene, mono- or polyfunctional substituted or unsubstituted cycloalkylene, mono- or polyfunctional substituted or unsubstituted $C_5$ to $C_{18}$ arylene or heteroarylene, mono- or polyfunctional substituted or unsubstituted $C_5$ to $C_{18}$ alkylarylene or alkylheteroarylene, mono- or polyfunctional substituted or unsubstituted $C_7$ to $C_{30}$ alkylene arylene; and, n is an integer.

3. Hydrolysis stable one-part self-etching, self-priming dental adhesive comprising (i) an acidic polymerizable (meth) acrylamide that comprises at least an organic or inorganic acidic moiety (ii) a polymerizable monomer (iii) polymerization initiator, inhibitor and stabilizer; wherein said polymerizable monomer is a mono-, bis- or poly(meth) acrylamide that is selected from the group consisting of:

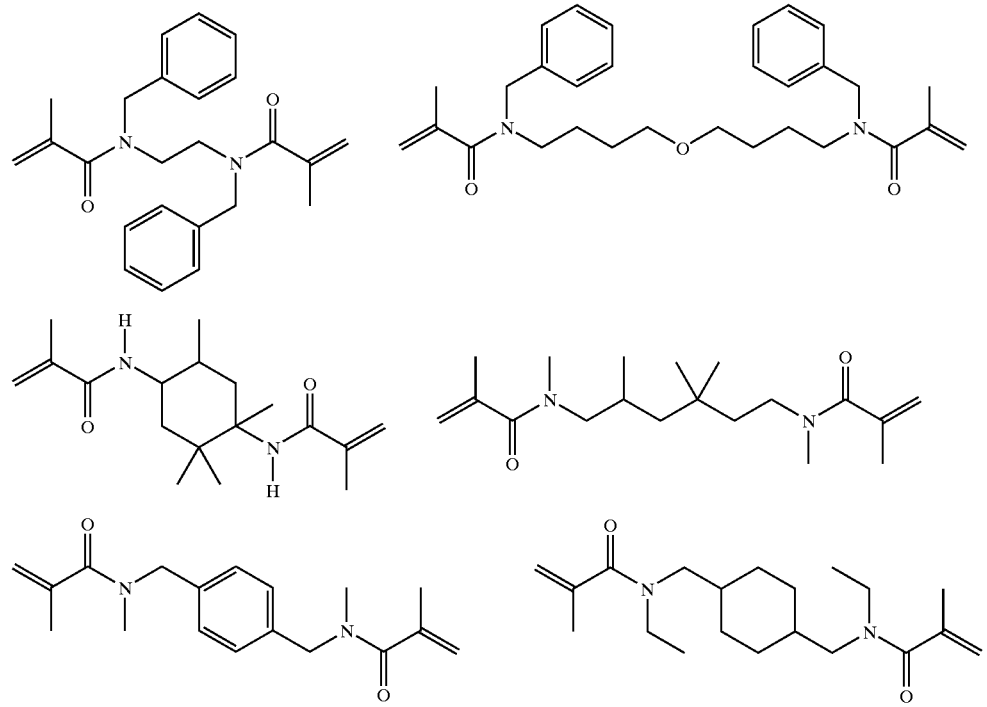

-continued
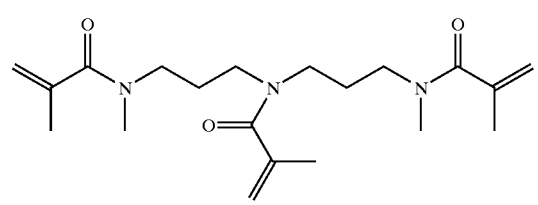
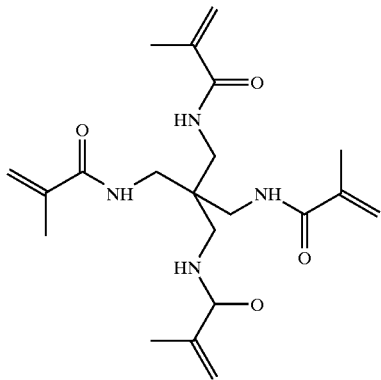
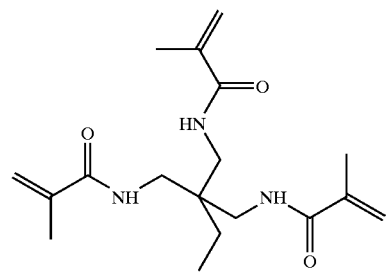
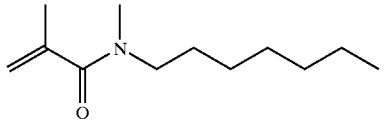
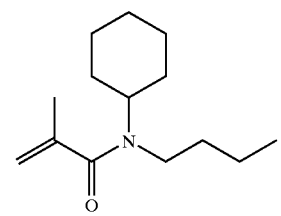
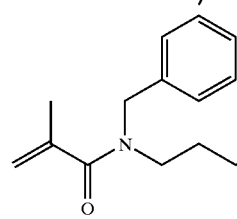
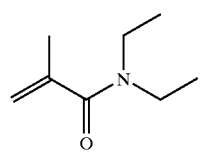
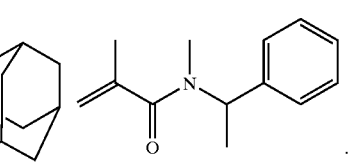
* * * * *